United States Patent [19]
Seney

[11] Patent Number: 5,275,558
[45] Date of Patent: Jan. 4, 1994

[54] DENTAL HANDPIECE, BUR MOUNT OPERATING SYSTEM

[76] Inventor: John S. Seney, P.O. Box 152, Sugarloaf Shores, Fla. 33044

[21] Appl. No.: 991,527

[22] Filed: Dec. 15, 1992

[51] Int. Cl.⁵ .............................................. A61C 1/12
[52] U.S. Cl. .......................................... 433/82; 433/84
[58] Field of Search ............... 433/82, 84, 85, 87, 433/104, 115, 132

[56] References Cited

U.S. PATENT DOCUMENTS

| | | |
|---|---|---|
| 3,125,809 | 3/1964 | White . |
| 3,324,552 | 6/1967 | Saffir .................. 433/82 |
| 3,778,904 | 12/1973 | Melde ................. 433/120 |
| 3,838,516 | 10/1974 | Borochaner ............ 433/84 |
| 3,871,097 | 3/1975 | Melde .................. 433/82 |
| 4,107,846 | 8/1978 | Fleer et al. ............. 32/27 |
| 4,359,317 | 11/1982 | Strohmaier et al. ..... 433/82 |
| 4,470,812 | 9/1984 | Martens et al. ........ 433/85 |
| 4,869,668 | 9/1989 | Seney .................. 433/85 |
| 5,022,857 | 6/1991 | Matsutani et al. ...... 433/85 |
| 5,055,043 | 10/1991 | Weiss et al. ............ 433/82 |
| 5,069,620 | 12/1991 | Matsutani et al. ...... 433/82 |
| 5,096,421 | 3/1992 | Seney .................. 433/82 |

FOREIGN PATENT DOCUMENTS

| | | |
|---|---|---|
| 395557 | 10/1990 | European Pat. Off. ............... 433/82 |
| 1092607 | 5/1958 | Fed. Rep. of Germany ......... 32/27 |
| 2852576 | 6/1979 | Fed. Rep. of Germany ...... 433/100 |
| 2829271 | 1/1980 | Fed. Rep. of Germany ........ 433/82 |
| 3734862 | 4/1989 | Fed. Rep. of Germany ........ 433/82 |
| 3734864 | 4/1989 | Fed. Rep. of Germany ........ 433/82 |
| 561537 | 5/1975 | Switzerland ........................... 433/84 |

*Primary Examiner*—John J. Wilson
*Assistant Examiner*—Nicholas D. Lucchesi
*Attorney, Agent, or Firm*—C. Hercus Just

[57] ABSTRACT

A dental handpiece provided with a handle and a head on one end thereof in which a turbine rotates at high speeds and accommodates a cutting bur having an axial through opening to direct a preferably hygienic coolant directly through the cutting end of the bur, while the opposite end of the bur, on the interior of the head, is highly polished and absolutely flat for rotating engagement with one surface of a rotary liquid seal including a seal member of very hard substance in combination with a pliable compressible member engaging the opposite surface of the seal member, the combination being housed within a recess extending upwardly in a push button on the head or other finger-operated bur release mechanism on the head and having coaxial fluid openings communicating axially with the through opening in the bur and fluid passage in the push button leading from a fluid supply conduit in the handle. The fluid preferably consists of one or more of several chairside selectable pharmaceutical ingredients added to a coolant for discharge into a cavity being cut in a tooth by the handpiece.

14 Claims, 6 Drawing Sheets

Section 6-6

DENTAL HANDPIECE, BUR MOUNT OPERATING SYSTEM

BACKGROUND OF THE INVENTION

The preparation of tooth cavities for acceptance of filling materials normally is a painful experience unless pain-relieving anesthetic drugs, such as Lidocaine injections, or nitrous oxide gas inhalation is first applied prior to the dental preparation. In conjunction with cavity preparation, it is customary for a dental assistant to spray a jet of water onto the tooth being cut by the bur of the handpiece and this frequently clouds or fogs the area being prepared so that the dentist has difficulty seeing where the cutting is occurring. Many modern handpieces operated at speeds up to 400,000 rpm in order that heavy cutting pressure is not required. However, at such speeds, heat can be generated up to 450° F. with a bur pressure of 32 grams, for example, at 170,000 rpm.

It has been found that a minimum water flow rate of 16 cc/minute is necessary to form a stream with force enough to reach the bur tip area in a commercial handpiece having as many as four or five jets of flushing water. This situation is responsible for such aforementioned fogging of the dental operation site.

Current types of handpieces which have axial through passages present difficulties when endeavoring to restrict cooling liquid by such liquid tending to enter the head and bearings of the turbine and flushes the lubricant thereof.

Another difficulty with such aforementioned through passages in burs in a handpiece is some community water supplies carry impurities and chemicals that may be harmful to patients and can clog the passage in the bur. Also, when using cooling sprays of water, when the dentist stops the flow water, there is a tendency for a suck-back or retraction function to occur in which contaminants in a patient's mouth may be drawn back into the head of the handpiece where they remain and may even migrate into the fluid supply conduits or hoses. Hence, when used with the next patient, any such contaminants can be discharged into said next patient's mouth.

SUMMARY OF THE INVENTION

It is one principal object of the present invention to provide a dental handpiece with, preferably special anti-corrosive and hygienic coolant, containing a special formula, which is discharged in water, solely through the longitudinal opening in the bur, while in most instances, some of the cooling liquid enters the interior of the head in the vicinity of the turbine, under which circumstances, the lubricant normally required by the bearings of so-called air-driven handpieces is flushed from the bearings or at least diluted by such water.

At present, most dental offices use ordinary tap water derived from community water supplies and therefore, it is subject to carrying impurities and chemicals that may be harmful to the patient and the internal turbine support bearings. When cooling or flushing operations are performed by the dentist, water flows under pressure from the source, through office piping and handpiece hoses or conduits through the handpiece and finally out the spray nozzle. When the dentist terminates the flow of water, a momentary suck-back or retraction action occurs caused by the collapse of the flexible delivery hose and, as such, has the real potential to suck in contaminants existing in the patient's mouth back into the nozzle orifice. Any bacteria are then capable of migrating back into the hose where, unless positively destroyed, may remain and multiply. Thus, when the next patient is treated and the water jet is used, the bacteria then existing in the water supply line are forced back through the handpiece and into the next patient's mouth.

It is the principal object of the present invention to provide a dental handpiece which includes means to direct cooling liquid, such as water or the special anti-corrosive coolant containing a special formula, comprising an aspect of the invention, which is discharged from the handpiece through a bur which is provided with a longitudinal axial passage between opposite ends to discharge either water or the special formula from the outer end of the bur directly to the interface between the bur and the tooth. Improved means also are included which are highly adequate to prevent the cooling liquid from reaching and/or mixing with the air turbine and the bearings thereof, details of which are set forth below.

To illustrate the present state of the art in which dental handpieces are provided with burs having axial passages between opposite ends of the bur, and means to direct cooling liquid thereto or therethrough, the following patents are cited as representative of the current state of the art on this subject:

| U.S. Pat. No. | | |
|---|---|---|
| | 3,125,809 - White | 1964 |
| | 3,324,552 - Saffir | 1967 |
| | 3,778,904 - Melde | 1973 |
| | 3,871,097 - Melde | 1975 |
| | 3,838,516 - Borochaner | 1974 |
| | 4,107,846 - Fleer et al | 1978 |
| | 4,359,317 - Strohmaier et al | 1982 |
| | 4,470,812 - Martens et al | 1984 |
| | 5,022,857 - Matsutani et al | 1991 |
| | 5,055,043 - Weiss et al | 1991 |
| | 5,069,620 - Matsutani et al | 1991 |
| European | 395,557 | |
| German | 1,092,607 | |
| German | 2,829,271 | |
| German | 2,852,576 | |
| German | 3,734,862 | |
| German | 3,734,864 | |
| Switzerland | 561,537 | |

The present invention comprises a modification or improvement over the inventions comprising the subject matters of applicant's prior U.S. Pat. Nos. 4,869,668, dated Sep. 26, 1989 and 5,096,421, dated Mar. 17, 1992.

It's another object of the present invention to provide a dental handpiece for use with a dental bur in which a longitudinal passage extends axially therethrough between the opposite ends thereof, the head of the handpiece supporting said bur, and is provided with longitudinal passages therein for discharging cooling liquid, cavity clearing air and air to drive the turbine within the head of the handpiece. Another important feature of the present invention comprises a rotary liquid transmission coupling mounted within the upper portion of the head of the handpiece and extending between the passage in the handle for cooling liquid and upper end of the bur inside the shaft of the turbine. Said coupling includes sealing means to prevent the leakage or migration of cooling liquid into the interior of the head in which the turbine, and especially the bearings therefor, are enclosed, whereby the normal lubricant for the bearings is not diluted or otherwise affected.

Another object of the present invention, as compared with applicant's prior patents, is to position said rotary transmission coupling in the upper end position of the head of the handpiece and comprises a stationary differential pressure-controlled rotary seal assembly consisting of a thin low-friction wear-resistant seal disc pressed against or integrated with an elastic and compressible circular member, which functions somewhat as a bellows, permitting limited downward or upward positioning of the seal disc in response to pressure of the coolant fluid against the fluid side of the disc and the opposing turbine exhaust back pressure existing inside the turbine housing which is controlled by an orifice in the exhaust discharge conduit. Thus, a self-regulating seal force is provided between the non-rotating stationary seal disc and the seal end of the rotating hollow bur that can compensate for possible variations that can occur in coolant and turbine air pressure changes, as well as variations in turbine mechanical loading.

Said above-mentioned mechanism provides a liquid-tight seal having fixed, very low drag load under all normal operating conditions, including operation where even standard non-hollow burs are used and when no coolant pressure is applied to the back side of the static disc seal. Under such circumstances, the disc seal contact force is reduced against the rotating bur by the turbine exhaust air pressure being higher than the coolant pressure.

Still another object of the invention, somewhat similar to applicant's prior patents, is to utilize burs which have the end opposite the cutting end super-polished and absolutely flat to effect a positive seal against the disc seal, whereby the present invention comprises a combination of the inner end of the bur, such as described above, and the foregoing details of the disc seal.

One further objective of the invention is to form said aforementioned stationary seal disc from low-friction, wear-resistant, self-lubricating materials, such as carbon compound P-658RC (Manufactured by Pure Industries, 441 Hall Ave., St. Mary's, PA 15857) and others such as Nylon, aluminum oxide, barium titinate, silicon carbide, tungsten carbide, quartz, sapphire, flint, agate, chrome plated copper, Teflon, Kevlar phenolic reinforced substrates, carbon fiber phenolic reinforced substrates and to seal the disc fluid tight to a flexible tube or bellows made from elastic materials, such as silicone rubber, natural rubber, synthetic rubber, etc. In this application the illustrated disc is formed from carbon P-658RC. The dimensions are: 0.020" thick, 0.125" diameter, with a 0.0150" diameter hole through the center. The seal face is optically flat and super-polished. The flexible member is tubular silicone rubber 0.125" OD, 0.060" ID and 0.035" long in sealing contact with or sealed to the carbon seal disc.

The rotary seal is formed by the rotary engagement of the super polished flat end of the hollow bur with said static seal assembly whereby minimum friction occurs between said relatively rotating surfaces of the polished end of the bur and the seal The principal purpose of the air-exerting pressure against one surface of the seal disc is to prevent undue friction between the polished inner end of the bur and seal disc, especially at the start-up of the turbine and until cooling liquid can be exerted against the opposite surface of the seal and discharge through the coaxial openings in the seal disc and the polished inner end of the bur and thereafter pass through the bur to the outermost end thereof.

Still another object of the invention is also to provide an additional 2-way liquid volume control valve, of a manually-operable nature, respectively in the lines for the cooling liquid to be supplied to the hollow bur or to liquid directed to the external jet on the head of the handpiece built in as an integral part of the handpiece handle assembly, or to both the hollow bur and external jet simultaneously, and permitting hand operation of the valve while drilling is in progress.

One further significant object of the invention is to extend hollow bur-type cooling to handpieces with push button bur-release mechanisms or other finger-operated quick-release mechanism. This necessitated the development of a rotary liquid seal invention that could be attached to the top of existing handpieces with quick bur-release mechanisms, such as push buttons or finger-operated levers.

A still further object of the invention is the incorporation of a coolant liquid purification system that is installed in the dental operatory that receives water from the municipal water source via the office water tap and subsequently deionizes the water and mixes a specially formulated coolant concentrate solution with the water and then purifies the combined solution which is then contained in a sterile reservoir. When the coolant flows to the handpiece through sterile plumbing, it discharges from the dental handpiece in sterile condition. Design features in this system prevent any bacteria from being sucked back into the handpiece coolant flow orifices, thereby preventing coolant contamination. This ensures the next patient will not be exposed to the previous patient's bacteria.

DETAILED DESCRIPTION OF THE PREFERRED EMBODIMENT OF THE INVENTION

The present invention primarily related to a dental handpiece and control mechanism therefor in which a continuous flow of cooling liquid travels through a longitudinal opening in the bur for discharge at the outer end thereof into the preparation formed in a tooth by said handpiece and bur at the interface between the tooth substance and the bur where heat is generated under normal operations. Laboratory measurements have disclosed that a bur when rotating at relatively high speed develops 5.88 BTU/min., which must be removed to prevent heat buildup. To evaluate the cooling effect of the invention, a dental drilling analyzer was developed to simulate and maintain reproducible tooth drilling conditions by so-called hollow dental burs through which cooling liquid is discharged.

EXEMPLARY DRILLING CONDITIONS

Bur speed: 170,000 rpm
Bur torque: 0.001655 foot lbs.
Bur tooth interface temperature without water after a thirty second running time: 480° F.
Bur tooth interface temperature: Continuous 86° F. using a flow rate of 1 CC/min. of 68° F. cooling water These data show that the method of utilizing cooling liquid in the present invention definitely prevents heat buildup in the operation of a dental bur. It reduces the water volume 16 times over the state of the art cooling methods and this improvement affords better operating visibility and higher drilling rates without heat-generated pain experienced by the patient or associated fear of tooth damage caused by excessive heating of the tooth structure by the drilling operation.

Because of the reduction of the amount of cooling liquid which is employed, flooding of the operating site is minimized or eliminated, because the small amount of cooling water leaving the tip of the bur is vaporized by the centrifugal force thereof and does not appear as liquid water in the highly turbulent area around the cutting bur, thus producing a mostly dry operating area with excellent visibility for the dentist and provides a major improvement over the present state of the art with respect to cooling methods for a dental bur.

The control mechanism, which is described in detail hereinafter, allows uninterrupted metered flow of cooling liquid, such as water, or special non-corrosive therapeutic cooling formulations, from a control cabinet through a rotary liquid seal in the head of the handpiece and then to and through the longitudinal opening through the bur and out the tip end of the bur. As might be expected, the rotary seal development employs relatively new technology which affords a substantially leak-proof operation at speeds even exceeding 400,000 rpm. with essentially zero drag in a space less than 0.125 inch diameter and 0.050 inch deep. The seal consists essentially of a rotary face, formed on the inner end of the bur, and mating static face in the form of a carbon disc with a 0.0150 inch diameter hole in its center and an elastic and compressible circular member which is either integrally sealed to or pressed against the back side of the disc seal to prevent coolant leakage and provide very limited upward or downward motion to the disc seal.

Some of the materials which are suitable for the elements of the seal comprise, in the bur: tool steel, 304 stainless steel, 430 stainless steel, tungsten carbide and other suitable materials that can be chrome-plated at the seal end.

In the stationary disc side, carbon compound P658RC and others, such as Nylon, aluminum oxide, barium titinate, silicon carbide, tungsten carbide, quartz, sapphire, flint, agate, chrome-plated copper, Teflon, KEVLAR phenolic (a product of DUPONT), and carbon-fibred phenolic. The preferred materials for the elastic back side of the stationary seal disc are silicone rubber, natural and synthetic rubber. The selection of the materials depends essentially on the operating speed and the minerals present in the cooling liquid, such as water.

Figure 1:
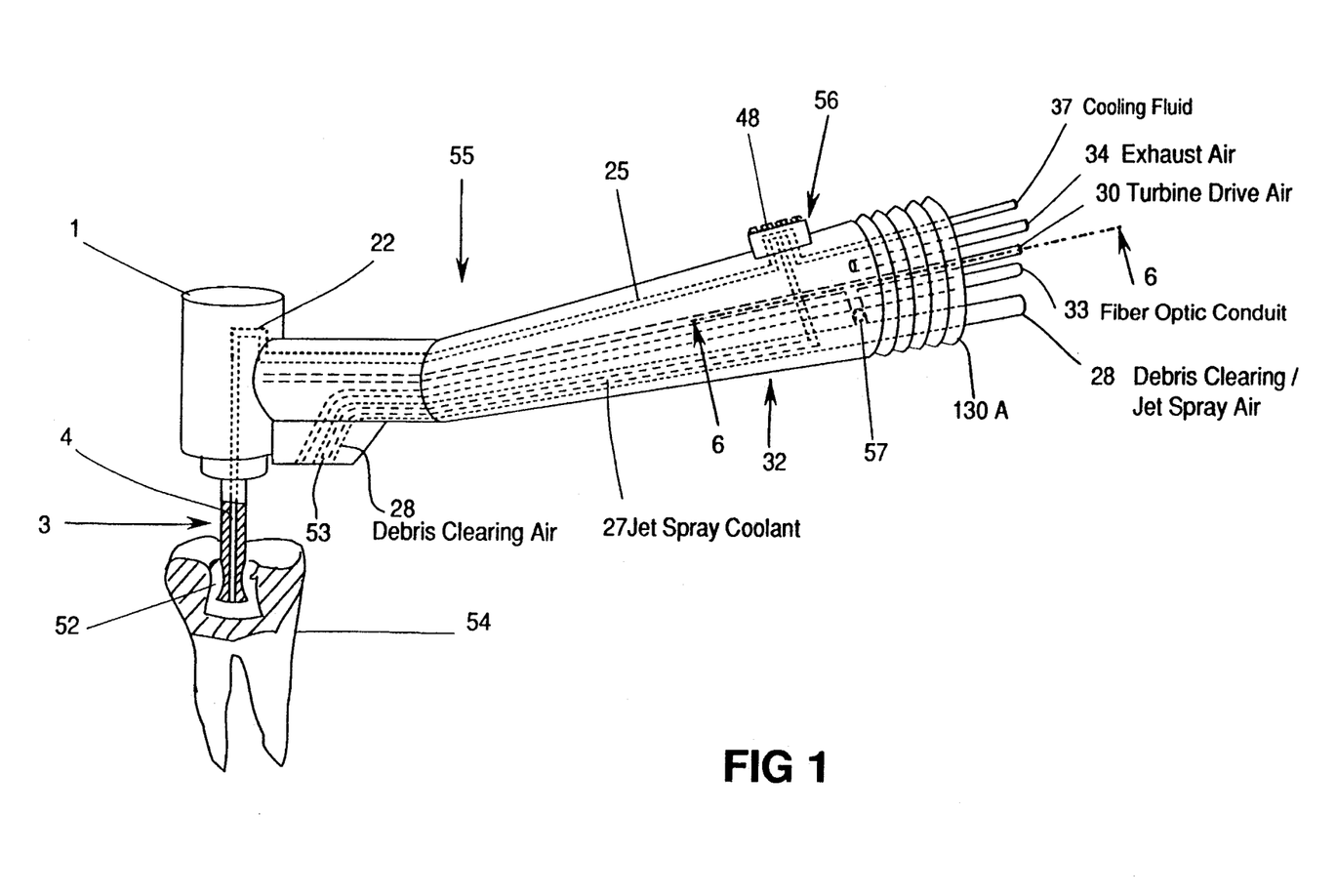
FIG. 1 is a perspective view of a handpiece embodying the invention and illustrating a bur on the handpiece extending into a partially-sectioned tooth, this figure also illustrating, in phantom, various conduits and tubes in the handle of the handpiece.
Figure 2:
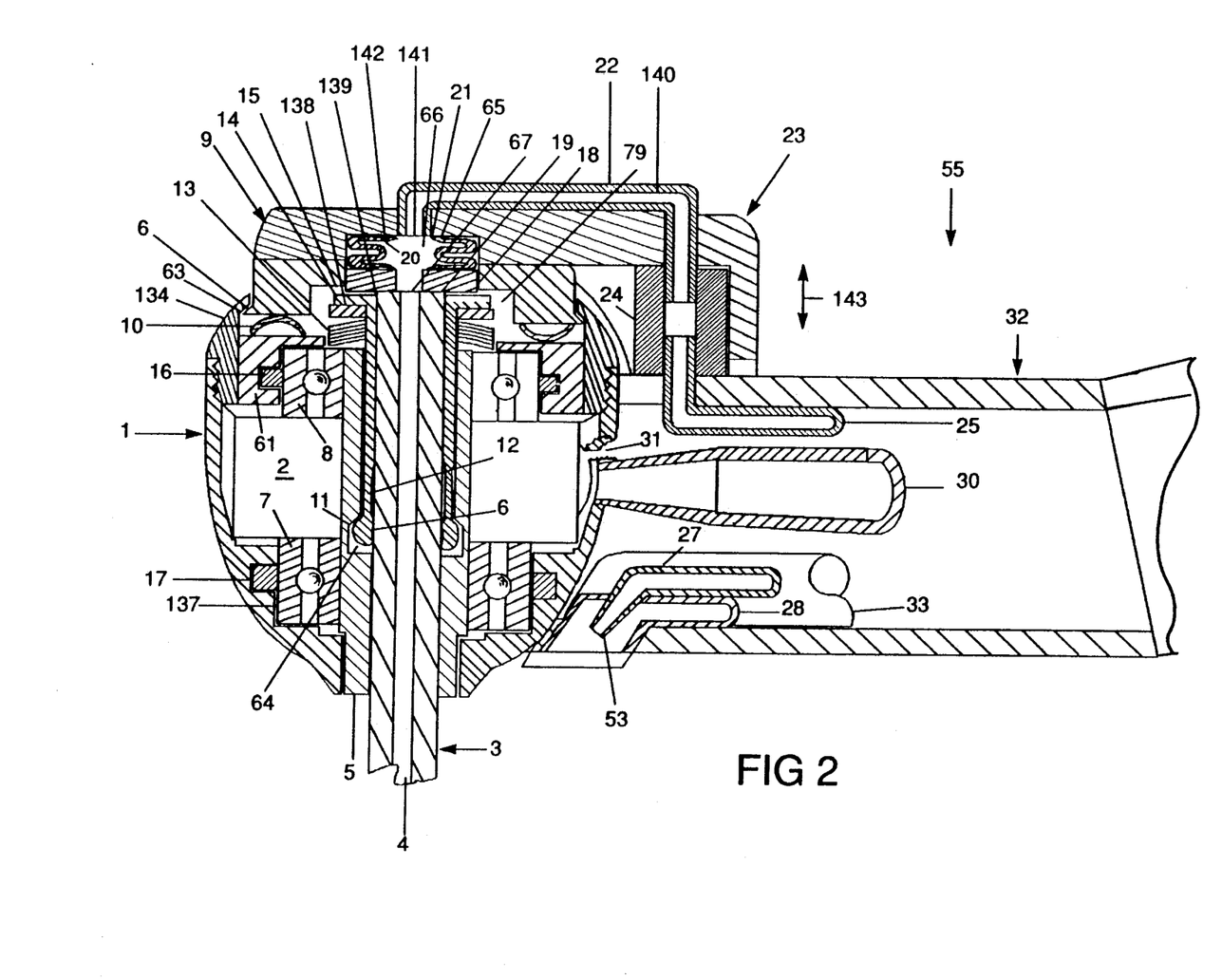
FIG. 2 is a vertically-sectioned view of the handpiece and a partial handle section in which fragmentary portions of air and water conduits are illustrated, this view showing the various elements contained in the head of the handpiece.
Figures 3, 5:
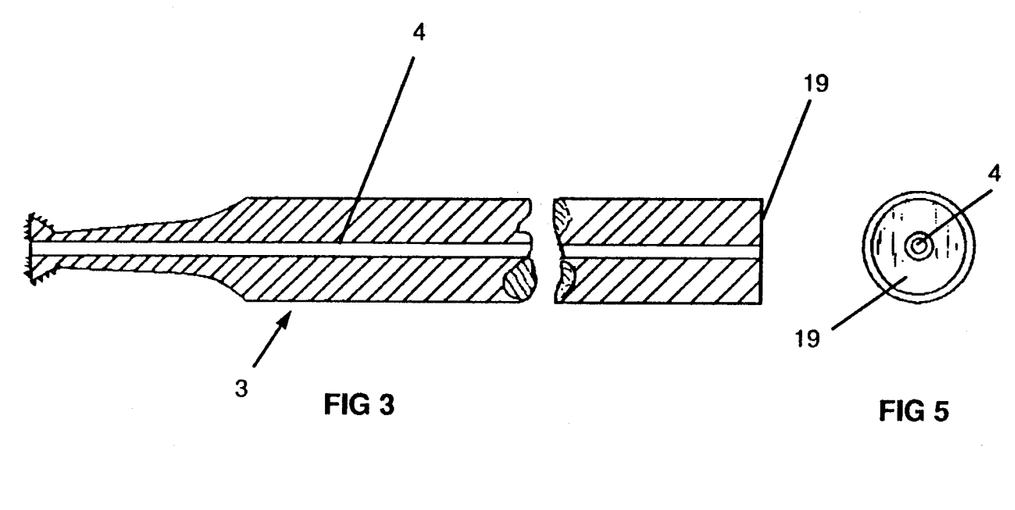
FIG. 3 is a longitudinally-sectioned view of a dental bur embodying the principles of the invention.
FIG. 5 is a plan view of the opposite end of the bur.
Figure 4:
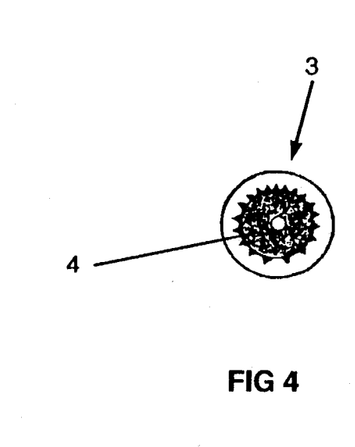
FIG. 4 is a plan view of the cutting end of the bur.

Referring now particularly to FIGS. 1 and 2 of the drawing there is illustrated a dental handpiece 55 which includes a handle 32 and a head 1, the axis of which is transverse to that of the handle. Extending from the lower end of the head 1 is a dental bur 3 through which a longitudinal passage 4 extends between opposite ends thereof, as best shown in FIG. 2. As shown in FIG. 1, the tip end of the bur has cutting blades which are shown in an exemplary cavity 52 in a tooth 54 in which the cavity is being shaped to receive a filling. The tooth and cavity are merely exemplary, as well as the bur.

The handle 32 contains a number of longitudinal passages which are shown in phantom in FIG. 1, these comprising a passage 25 through which cooling liquid is furnished for discharge from the longitudinal passage 4 of the bur. Also, the outermost end of the passage 34 shown in FIG. 1, is exemplary of exhaust means for turbine driving air exiting handle 32 after having exited the turbine, which rotates within the head 1 via turbine exhaust discharge port 31 as shown in FIG. 2. A passage 30 is the means by which driving air, under pressure, is delivered to the head of the handpiece to operate the turbine 2, which is shown in detail in FIG. 2. Still another passage 37 receives cooling fluid from a suitable reservoir at the outer end thereof and directs the same to the common port 38, see FIG. 6, of 2-way valve 56 and exits through said 2-way valve 56 through outlet ports 39 and 40, shown in FIG. 6, if the valve is in the neutral position, or through port 39 only, if the valve is in the full clockwise position, or through port 40 only if the knob 48 is in the full counterclockwise position.

A fixed dial position stop is provided by a fixed stop screw 45, located in a semicircular slot 44 in the knob 48. If the valve is in the required clockwise position, as viewed in FIG. 6, coolant will flow into line 27 and exit the jet spray nozzle 53, see FIG. 2, where it will be atomized by air flowing through line 28 from one-way air passage 57 connected to the turbine high pressure supply passage 30. A secondary air supply not shown, is attached to line 28 at male coupling 130, see FIG. 8, which is controlled by a foot-operated valve 58, shown in FIG. 8. The turbine is driven from air controlled by a foot-operated valve 59. This turbine air pressure also operates a pneumatically-operated coolant flow control valve 60 that supplies coolant to male connection fitting 37, shown in FIG. 8, which supplies coolant to the common port of the 2-way valve 56.

When turbine air is shut off, the coolant to the handpiece also is shut off by valve 60. At this point of operation, the dentist can operate the other foot-operated valve 58, shown in the lower part of FIG. 8, and apply air pressure to line 2 to direct air only out of the jet spray nozzle 53, see FIG. 2, for blowing drilling debris from the cavity 52 and drying the cavity for further filling operations. Air pressure applied to line 28 closes the 1-way ball check valve 35, see FIG. 6, in passage 57 to prevent air from entering line 30 and inadvertently driving the turbine during this operation. The counter-clockwise position of valve 56 in FIG. 6 applies coolant to port 40 and into line 25 through resilient coupling 24, see FIG. 2, into upper coolant transfer line 22 through elastic seal 20 and the center hole 67 in stationary seal disc 18 and then into the longitudinal bore 4 of the hollow bur and out the cutting bur end onto the tooth cutting face.

The integral turbine 2 is mounted, by a press fit or other wise, upon a tubular shaft 5 upon which the inner races of a spaced pair of antifriction bearings 7 and 8 are mounted. The outer race of the top bearing 8 is mounted in a support ring 61 that is press-fitted into the bearing cap 134. The outer race of lower bearing 7 is mounted in the lower bearing support bore 137 inside the handpiece head. Both outer races of said bearings are shock mounted in their respective bores by silicone rubber "O" rings 16 and 17, which are square or nearly square in cross-section. The top bearing support ring 61 supports a resilient cup washer ring 10 that biases the push button cap 9 upward against conical tapered bore 63 that engages a like mating surface 62 laterally extending from the push button cap 9.

The push button-actuated chuck in the handpiece is shown as unit 14, consisting of a hollow tubular structure 12 with a flat flanged top and a segmented lower end 12 that has a larger lower diameter than the bore in the turbine shaft. A chucking easement groove 64 in the bore in the turbine shaft is provided to allow the flexible enlarged outer diameter segments 12 to snap into groove 64 to allow the inner bore of the chuck to assume the same internal diameter as the outer diameter of the bur, thereby permitting the bur to be easily seated or withdrawn from the chuck. A stack of cup washer springs 13 is installed between space washer 138, which contacts the upper flange of chuck 14 and the turbine shaft 5 to cause the chuck 14 to be forced upward. Upward movement of chuck 138 forces the enlarged chuck spring segment ends 12 to engage the upper tapered edge 11 of the groove 64, thus causing an inward force to the segmented chuck jaws, and thus causing chuck holding jaws 6 to tighten around the bur 3 and locking it to the turbine shaft 5.

A face 15 on the push button cap is separated from face 139 on the chuck 0.020" when no pressure is applied to the push button. Downward pressure applied to the push button overcomes the pressure of cup washer 10 and allows a pressure contact to be made between the chuck contact face 139 and cap engagement face 15, thus overcoming the spring tension of cup washer springs 13, allowing the chuck to move to a lower position in the turbine shaft permitting the chuck segments 12 to retreat back into groove 64 and thus, releasing the bur from the bur-holding jaws 6 for removal or installation.

One of the outstanding improvements afforded by the present invention comprises a rotary liquid transmission seal 65, the primary elements of which comprise a disc seal. The principal preferred materials from which the seal is made are set forth above. The two-part seal can be an integrated carbon disc and elastic compressible member or two separate parts compressed together during operation. This composite unit has a central opening in each member and is mounted intermediately between a relatively flat face 142 in the inner end of a central recess extending upwardly into the cap and into which the superpolished and absolutely flat innermost end of the bur extends, as clearly shown in FIG. 2. The push button 9 also includes a radial passage 140 which at one end extends into the recess 21 and furnishes cooling liquid to recess 21. The seal disc 18 also has a central opening 67 which is coaxial with opening 141.

Figure 6:
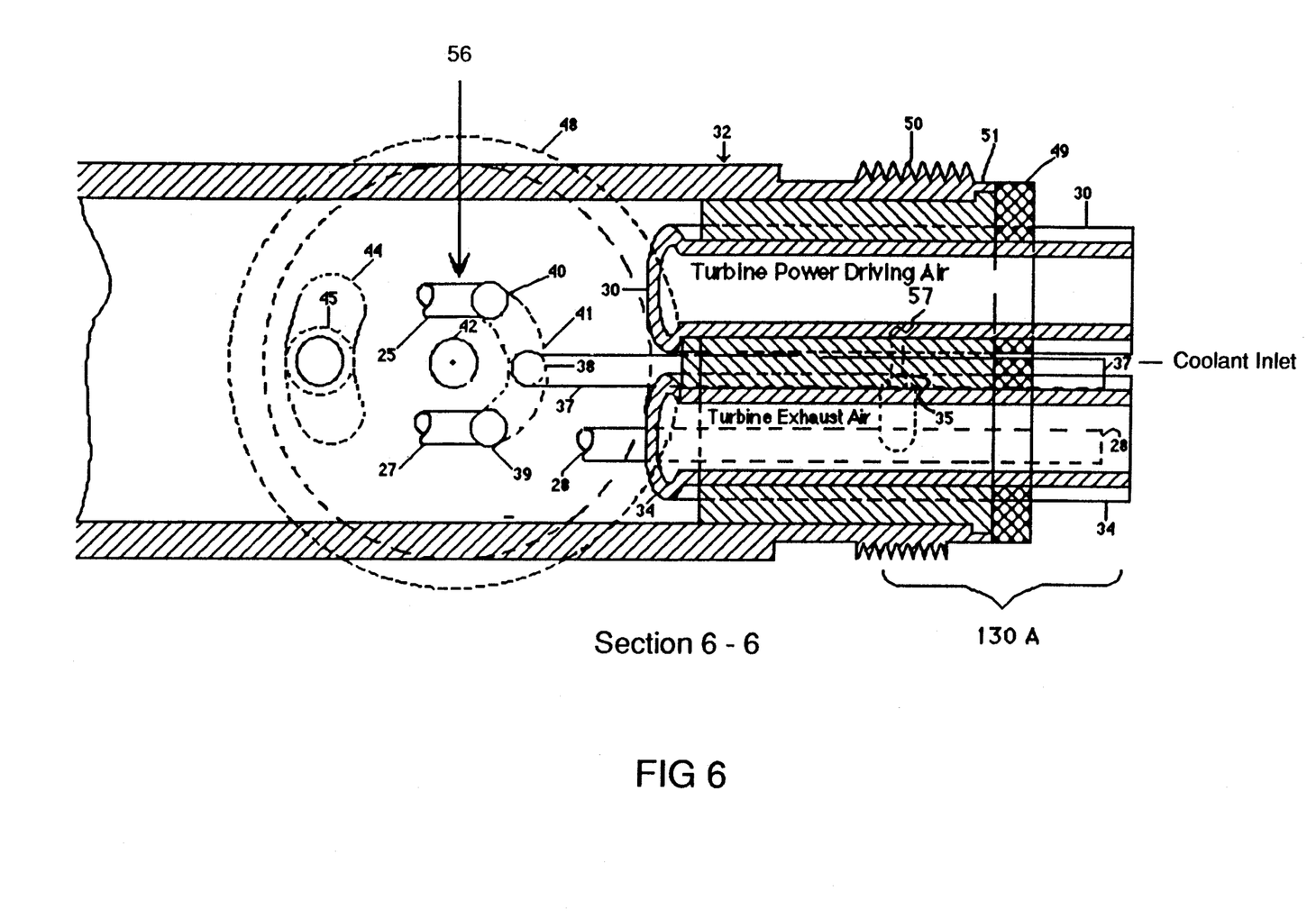
FIG. 6 is an enlarged fragmentary longitudinally-sectioned view of the area of the 2-way valve on the handle of the handpiece, as seen on the line 6—6 of FIG. 1.
Figure 7:
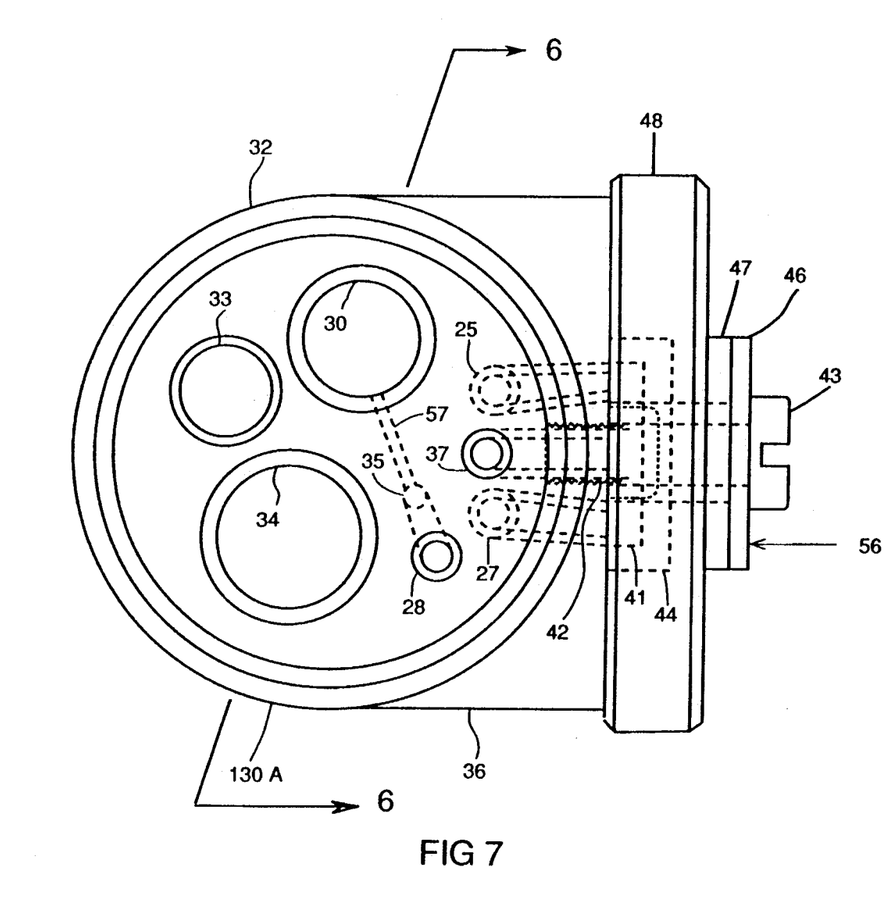
FIG. 7 is an enlarged outer end view of the handpiece showing, in full lines, the terminal ends of certain conduits and tubes within the handle and, in phantom, showing conduits associated with the 2-way valve on the handle.

Cooling liquid or fluid is furnished to radial passage 140 on push button 9 from passage 25 in handle 32, which is connected to passage 140 by coupling 24. The 2-way valve 56 on handle 32, when in one position, controls flow of cooling fluid in passage 37 for delivery to the central passage of the bur. As shown in FIG. 6, there is a sealing gasket 49 on the outer end of the handle through which the various conduits and passages extend. Since the push button 9 must have limited movement along its axis relative to the head 1, the flexible resilient coupling 24 is provided relative to passage 25 in handle 32 and provides leakproof flow of coolant liquid through said passages.

The rotary liquid transmission coupling comprises the innermost end 19 of rotary bur 3, which preferably is formed from any selection of tool steel, 308 stainless steel, 430 stainless steel tungsten carbide or other suitable materials that can be chrome plated at the seal end. All of these have good wear and sealing characteristics, especially when used in contact with the seal disc 18 when it is formed from self-lubricating compounds, such as carbon compound P658-RC. The bur 3 also has a central longitudinal passage 4 extending entirely therethrough which is coaxial with openings 67 and 141 and serves to communicate with the longitudinal passage 4 in the bur 3.

For the most effective sealing between the inner end of bur 19 and seal disc 18, it is essential that the end 19 be super-polished and optically flat. The term super-polished means that there must be no roughness in excess of 0.001 micro inch. The material from which the bur is made must be corrosion-resistant relative to the cooling liquid. The bur must also be dynamically balanced on the central axis so that there is no vibration when rotating, especially at high speeds, and the bur must meet critical high speed cutting tool safety standards. From the foregoing, it will be seen that the surface 19 is precise and ensures smooth movement relative to the stationary innermost surface of the seal disc 18.

Figure 8:
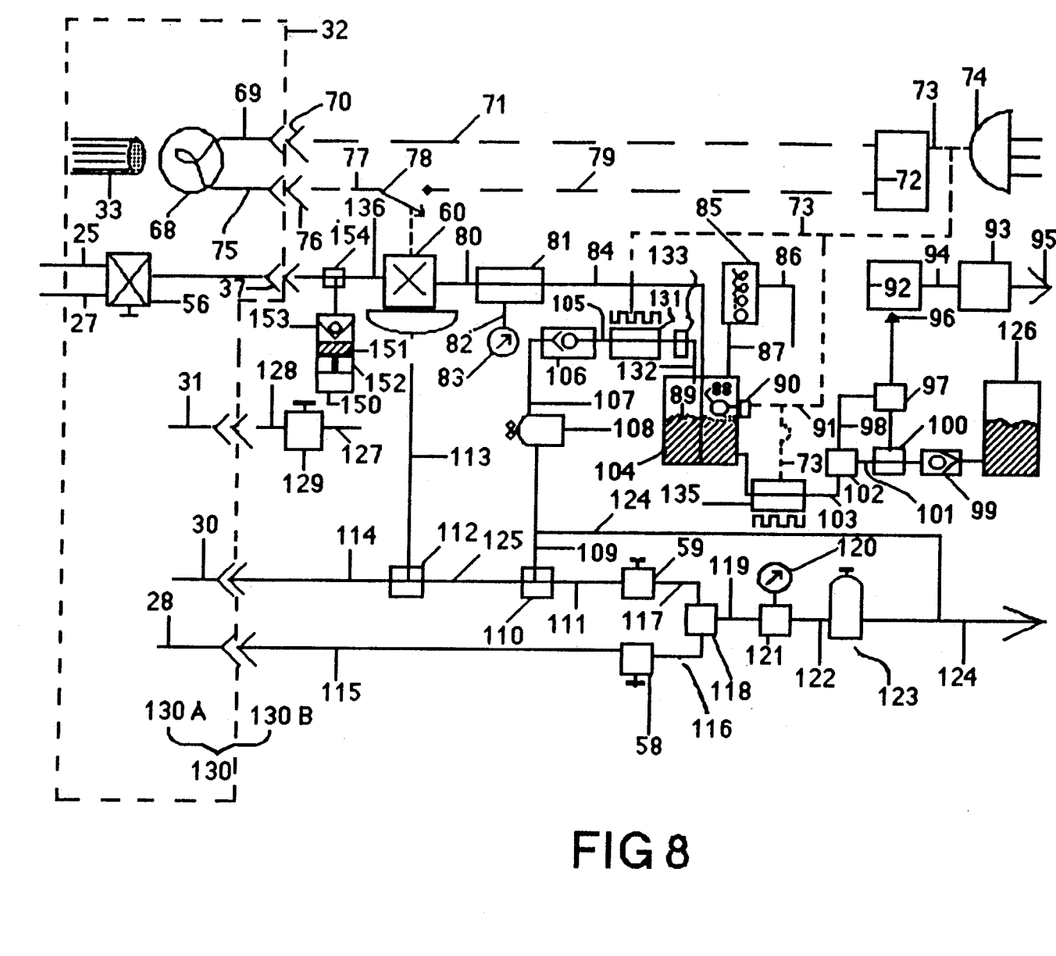
FIG. 8 is a diagrammatic view of all control mechanism for the various components of the system for controlling the supply of air, water and solutions delivered to the head and bur held by said head and by which the handpiece is operated.

The operation of the rotary liquid coupling also is dependent upon a special ratio of turbine exhaust air back pressure which is controlled by back pressure control valve 129, shown in FIG. 8, in the exhaust conduit that permits exhaust air to escape and maintain exhaust air pressure within the annular space 79 in the junction of the handle and head.

The operation of the rotary liquid transmission coupling is as follows: Back pressure is effected by the pressure of cooling liquid within the recess 21 as received from radial passage 140 through opening 141 and is exerted against the upper surface of seal disc 18, as viewed in FIG. 2, while exhaust air under controlled pressure is furnished to annular space 79 and exerts pressure against the lower surface of seal disc 18. The air and liquid pressures preferably are regulated so as to exert substantially equal pressure against opposite surfaces of the seal disc and thereby maintain the inner super-polished end 19 of the bur in close contact with the adjacent surface of the seal disc. This is especially desirable upon turbine start up so that frictional contact will not cause over-heating between the relative static and rotating surfaces of the seal disc and super-polished end of the bur. When steady operation of the turbine occurs at high speeds, no appreciable friction will be generated between the engaging surfaces and the temperature of the cooling liquid likewise is present to effect cooling of the two relatively movable surfaces.

CONTROL SYSTEM FOR AIR AND LIQUIDS

The control mechanism by which driving air is applied to the turbine in the head of the handpiece and the coolant formulation, volume, and pressure control are critical to the hollow bur drilling and cutting system, as well as the clearing of debris from the tooth cavity and supply drying air to the prepared cavity. Laboratory testing has shown that a noncorrosive coolant must be used since many city and community water system's supply to dental offices contain minerals, bacteria and other elements that can corrode and dull the sharp edges of burs, plug and clog piping and tubing and corrode delicate handpiece components. Therefore, special care must be taken to provide a coolant and a delivery system therefor that is compatible with this invention of hollow bur cooling. The drawing in FIG. 8 illustrates the hollow bur handpiece supply and control system. Two types of systems have been developed. One is a small portable package having all the functions, as shown in FIG. 8, except it uses a sterile pre-bottled formulated coolant supply in a 1 liter or other compatible size of screw top bottle.

The second system uses a tap water purification and deionization process fed from the dental office commercial water supply. Pre-bottled prescription additives and the purified water are pumped by pressurized metering pumps adjusted to their proper mixing ratio, then injected through an inline mixer and then through inline sterilizer and then into a pressurized common dental office coolant reservoir that furnishes sterilized coolant to one or more operatories. Laboratory tests have demonstrated that when cutting laterally or longitudinally in a tooth while using hollow bur cooling only, that the drilling site temperature is approximately 6° F. cooler using the following alcohol-based coolant than when using water as the cooling medium:

| COOLANT CONCENTRATE | FORMULAS Percentages | COOLANT |
|---|---|---|
| Sodium Benzoate | 0.9% | 88.9% Water |
| Glycerol | 27.0% | 11.1% Concentrate |
| Ethyl Alcohol | 71.0% | |
| Flavoring | 1.1% | |

(Water to Coolant Concentrate Ratio = 8.009:1)

Referring to FIG. 8, electrical power is supplied by plug 74 through line cord 73 to power supply 72 that converts 120 volts/60 Hz input to 3.8 volts direct current output to supply power to the lamp that provides light to illuminate the fiber optic light projection elements 33 in the handpiece. The positive terminal of the power supply is connected by line 71 to plug 70, thence to line 69 in the handpiece cable to one terminal of lamp 68, located in the female half of coupling 130.

Line 79 connects the negative terminal of power supply 72 to the normally open contact of pneumatically-operated switch 78; thence from the common contact of switch 78 via line 77 to plug 76 and thence through line 75 to the negative terminal of the lamp.

The switch 78 closes and turns on lamp 68 each time air pressure is applied to drive the turbine in the handpiece. The coolant is composed of pure water and chemical additives that are measured and mixed in the proper ratio. In one formulation the ratio is 88.9% water and 11.1% concentrate. The concentrate is composed of Ethyl Alcohol (71%), Glycerol (27.0%), Sodium Benzoate (0.9%) and flavoring, such as peppermint, spearmint or other pleasant-smelling and tasting deodorants (1.1%) or other prescription elements the doctor may prescribe.

The system is connected to water supply 95 through filter 93 to the water purification unit 92 via line 94 wherein the water is deionized and treated to remove all corrosive elements. The purified water passes through one-way check valve 96 to the inlet of electrically-driven positive displacement metering pump 97, thence via line 98 to one port of fluid-mixing element 102. The vessel 126 contains the concentrated additive solution. The discharge port of vessel 126 is connected to the electrically-driven metering pump 100 via one-way check valve 99. The discharge from pump 100 is connected to the other inlet port of the fluid mixing element 102 via conductor 101.

The mixed solution at the outlet port of mixer 102 is connected to the inlet of an electrically-heated heat-recovery type heat-exchanger coolant-sterilizer having a high point temperature of 275° F. Boiling of the coolant at this temperature is prevented by maintaining the coolant pressure at 30 psi gage which is above the coolant vapor pressure for 275° F. Because this is a heat-recovery type heat-exchanger, the heat of the coolant at its high point of 275° F. is removed and exchanged into the incoming coolant flowing into the inlet of the sterilizer. Therefore, the coolant discharge of the sterilizer is at about room temperature. However, the discharged coolant has reached a temperature of 275° F., which is sufficient to kill all bacteria and destroy viruses that may have been present in the incoming coolant, thus the coolant is sterilized by unit 135 and thence to coolant supply reservoir 104 through line 103. The coolant solution in reservoir 104 is maintained at the operating fluid level 89 by float 88 that operates an electrical "ON/OFF" switch 90. Electric line 73 furnishes electric power to the fluid level control switch 90 which turns ON or OFF the two metering pumps 97 and 100, which supply the fluids to reservoir 104 and maintain a constant coolant level in the reservoir 104. The air above the fluid level in the coolant reservoir is maintained at a constant pressure of 30 lbs. gage.

In the coolant supply system for multi-office use, 100 psi air supply is connected via line 124 to the inlet port of the coolant pressure regulator 108. Regulator 108 maintains this air at 15 psi gage. Line 107 connects the air at 30 psi to one-way valve 106, thence through it to a heat-recovery multi-pass heat exchanger 131, wherein the air flowing through it reaches a high temperature of 275° F. At this point, the air returns its heat via air cooler 133 to the incoming air and exits at room temperature. The exit air is now sterile and is injected into the reservoir 104 via conduit 132.

A pressure relief valve 85 is connected via line 87 to the top of the coolant reservoir 104. The relief valve 85 is set to open on pressures over 35 lbs. gage The discharge is directed to the atmosphere via line 86. Cooling fluid exits reservoir 104 via line 84 to tee 81, through tee 81 to conduit 80 and into pneumatically-controlled coolant flow valve 60 and through the same via conduit 136. Positive displacement hypodermic-type dispensing pump with variable precision electronic drive injection rate control 150 dispenses concentrated sterile prescribed fluid 151 for hypodermic syringe 152 into line 136 via check valve 153 and tee 154. Coolant now containing prescribed pharmaceutical fluid flows into male plug 37 that furnishes coolant mixture to the common port of 2-way valve 56 in the handpiece. The coolant pressure gage 83 connected to the coolant supply line via line 82 is used in conjunction with regulator 108 to adjust collant pressure.

Turbine drive air is adjusted to 30 psi gage by air pressure regulator 123 which is attached to the 100 psi operatory air supply via line 124. The 30 psi gage air is indicated by pressure gage 120 attached to line 122 via tee 121. Air at 30 psi gage passes through tee 121 into line 119. The line 119 is split by tee 118 providing 30 psi air to enter foot-operated normally-closed valve 59 via pipe 117. Air control valve 59 passes air at 30 psi to tee 110. In single office use, where bottled coolant is used, the bottled coolant bottle is substituted for reservoir 104. In this case, the coolant pressure regulator is fed from the 30 psi line tee 110 via line 109, and line 124 is not used.

Line 125 connects tee 112 with tee 110. Line 113 connects tee 112 to the cooling fluid pneumatically-operated and normally-closed valve 60 and normally-open switch 78 assembly. Thus, when the foot-operated valve 59 is operated, coolant can flow to the handpiece and the light 68 will turn ON and turbine drive air at 30 psi will be connected to the male plug 30 of the handpiece via line 114 and the turbine will run. Air to clear the cavity of debris and to dry it for inspection and filling is obtained from the foot-operated normally-closed valve 58, which is fed from the tee 118 at 30 psi pressure via line 116. Foot-controlled clearing air is provided to the male plug 28 on the handpiece handle via line 115.

The foregoing description illustrates preferred embodiments of the invention. However, concepts employed may, based upon such description, be employed in other embodiments without departing from the scope of the invention. Accordingly, the following claims are intended to protect the invention broadly, as well as in the specific forms shown herein.

I claim:

1. A dental handpiece of the air-turbine type comprising in combination,
   a. an elongated handle having fluid conducting passages therein connected respectively at one end to cooling and flushing fluid and turbine-driving air under pressure,
   b. a hollow head connected to the other end of said handle and having passages therein for said fluid and air under pressure,
   c. a turbine mounted upon anti-friction bearings in said head respectively in axially-spaced relationship, said turbine having a central generally tubular shaft open at opposite ends and said passage for air under pressure being directed to said turbine in a manner to rotate it preferably at high speeds,
   d. a dental bur having an axial opening extending between its opposite ends and supported releasably and axially within said tubular shaft of said turbine in a coaxial manner, inner end of said bur extending a limited distance beyond the inner end of said shaft and said inner end of said bur being highly polished and absolutely flat,
   e. a rotary liquid seal device in an upper part of said head comprising a rotary seal disc of extremely hard composition having one highly polished and absolutely flat surface in abutting rotary engagement with said flat inner end of said bur, a central opening therein for fluid passage, and
   f. a pliable compressible member having a central opening and abutting an opposite surface of said seal disc in said head and the opening in said seal disc communicating with one of said passages in said head that is connected to a source of flushing fluid, whereby said fluid can be delivered through said opening in said pliable member to the inner end of said axial opening in said bur to cause cooling fluid to be discharged from the opposite end of said bur to a tooth preparation.

2. The dental handpiece according to claim 1 further including a manually-engageable push button mounted upon the upper end of said head and mounted for axial movement downward on said head, said push button having a recess extending upwardly into it and supporting said pliable member and rotary seal disc therein for engagement with the inner end of said bur.

3. The dental handpiece according to claim 2 wherein said tubular shaft of said turbine has a chuck extending axially within it and surrounding said bur, said chuck having a flat circular flange on the upper inner end thereof extending transverse to the axis of said chuck and including elastic members having means thereon interengageable with means in said chuck to urge said members into gripping engagement with said bur when said chuck is moved axially upward in said head, spring means operable to move said chuck to grip said bur, and the push button being operable when moved inward to move said elastic members on said chuck in a direction to release said bur for removal from said head.

4. The dental handpiece according to claim 3 in which said push button, when pushed inward relative to said head, is operable to press said pliable compressible member and said seal member against the inner end of said bur when clamped in said chuck and move the chuck downwardly against the action of said spring means, whereby said chuck release its clamping action upon said bur and effects release thereof from said head.

5. The dental handpiece according to claim 2 in which the uppermost anti-friction bearing has a mounting ring in said head and said head also has additional spring means disposed between said mounting ring and said push button operable normally to maintain said push button or other bur-release means removably in an elevated position.

6. The dental handpiece according to claim 1 further including an operating and control system connected by pliable conduits to an outer end of said handle of said handpiece and including a 2-way valve mounted on said handle at a convenient manual manipulating location and including a knob supported on said valve for limited rotation selectively between two positions respectively to deliver fluid for discharge through said bur or to discharge fluid as a spray directed from said handle toward the cutting end of said bur or discharging fluid through both the bur and spray from the handle concurrently.

7. The dental handpiece according to claim 6 in which said operating and control system includes a sterile coolant supply system adapted to operate upon tap water in a manner to ionize and demineralize said water or prescribed coolant concentrations with water to store the same for delivery to the dental handpiece to maintain the fluid-containing conduits germ-free.

8. The dental handpiece according to claim 1 wherein said pliable compressible member is operable to permit limited downward or upward positioning of the rotary seal disc in response to pressure of said cooling fluid against a fluid-engaging surface of said disc and opposing back pressure resulting from turbine exhaust, whereby a self-regulating seal force is provided between the seal disc and the flat inner end of the bur, thereby minimizing wear of the co-engaging surfaces of the flat inner end and the seal disc.

9. A dental handpiece comprising in combination,
   a. a elongated handle having fluid and air passages therein extending to a head mounted on one end of said handle,
   b. a rotary a dental bur, air-driven turbine having an axial bore therein and supported within said head by anti-friction bearings and operated at high speed by compressed air supplied through said handle to said turbine,
   c. a chuck within said bore and operable to secure said bur in operative position within said shaft, said bur having an axial passage therein between opposite ends,
   d. a push button mounted upon an upper portion of said head selectively for downward movement toward an inner end of said bur, and said push button having a recess extending centrally upward from a lower surface thereof immediately above the inner end of said bur, a conduct for cooling fluid extending from said handle and a supply thereof to a central opening in an upper end of said push button and terminating in said recess to communicate with said axial passage in said bur, and
   e. a yieldable compressible member mounted in an upper end of said recess in said push button and a stationary rotary seal member also within said recess and abutting said compressible member, both said compressible and seal members having central openings aligned with said conduit for cooling fluid, and said seal member flatly abutting the inner end of said bur for rotation against said seal member to permit cooling fluid to discharge from a cutting end of said bur with complete freedom from leakage of fluid when said handpiece is operating.

10. The dental handpiece in accordance with claim 9 further including means to connect one of said passages in said handle which delivers coolant fluid to the bur of said handpiece comprising conduit means therefrom to a reservoir containing sterile coolant solution concentrate comprising operable proportions of sodium benzoate, glycerol, ethyl alcohol and a limited amount of flavoring, said concentrate serving to maintain the handpiece and conduits sterile, said concentrate being mixed with water in use, in predetermined proportions.

11. The dental handpiece in accordance with claim 10 in which the formula for said coolant concentrate is:

| | |
|---|---|
| Sodium Benzoate | 0.9% |
| Glycerol | 27.0% |
| Ethyl Alcohol | 71.0% |
| Flavoring | 1.1% | which is mixed with water in proportion of:
11.1% concentrate and 88.9% water to form a coolant solution.

12. The dental handpiece in accordance with claim 9 further including means to inject into the coolant conduit precise amounts of pharmaceutical/medicinal concentrates specifically tailored for individual patient requirements, such as, but not limited to: anti-cavity fighting agents such as fluoride, tooth surface adhesive preparations for creating a strong bond between tooth and filling, anti-bacterial agents to kill bacteria accumulating in a patient's mouth and prevent further decay after filling, prescription drugs tailored to individual patient requirements when allergic situations occur, and nerve-deadening agents to prevent pain.

13. The dental and piece in accordance, with claim 9 further including a mixer for said fluid having a discharge therefrom connected to the inlet of an electrically-heated heat-recovery type heat-exchanger coolant sterilizer having a high point temperature of 275° F., whereby boiling of the coolant at said temperature is prevented by maintaining the coolant pressure at 30 psi gage which is above the coolant vapor pressure for 275° F., whereby because a heat-recovery type heat-exchanger is used, the heat of the coolant at its high point of 275° F. is removed and exchanged into the incoming coolant flowing into the inlet of the sterilizer.

14. The dental handpiece according to claim 13 wherein, due to the high point of temperature of the coolant of 275° F., all bacteria and viruses which may be in the coolant are destroyed.

* * * * *